United States Patent [19]
De Matthaeis

[11] Patent Number: 6,024,092
[45] Date of Patent: Feb. 15, 2000

[54] INFLATABLE PROCTEURYNTER FOR TREATMENT OF ANAL SPHINCTER PATHOLOGIES

[76] Inventor: Marina De Matthaeis, Via Poli 48, 00187 Rome, Italy

[21] Appl. No.: 08/798,763

[22] Filed: Feb. 11, 1997

[30] Foreign Application Priority Data

Feb. 14, 1996 [IT] Italy ................................ TS960004 U

[51] Int. Cl.[7] .................................................. A61F 5/48
[52] U.S. Cl. ................................... 128/885; 128/DIG. 25
[58] Field of Search .................................. 128/846, 885, 128/DIG. 25; 600/29–31; 604/347–353

[56] References Cited

U.S. PATENT DOCUMENTS

| | | | |
|---|---|---|---|
| 2,324,520 | 7/1943 | Lamson | 128/DIG. 25 |
| 4,471,782 | 9/1984 | Shuffield | 128/898 |
| 4,553,533 | 11/1985 | Leighton | 128/885 |
| 4,710,169 | 12/1987 | Christopher | 604/349 |

*Primary Examiner*—Michael A. Brown
*Attorney, Agent, or Firm*—Browdy and Neimark

[57] ABSTRACT

The invention is of valid use in the field of the treatment of anal sphincter pathologies, especially for the treatment of fissures and sphincter hypertonia. The procteurynter in question consists of a bag (1) made of plastic material and a sheath (2) that is internally crossed by two tubes: one tube (3) for the flow of water or air and a second tube (4) for the eventual introduction of an ultrasonoscope. Once the bag (1) is filled with water or air through the holes (2.6) made in the wall (2.5) of the sheath (2), it takes on an hourglass shape: two cones with a central neck or constriction.

The distal part of the sheath (2) has a plug (2.3) inside it to completely occlude the internal lumen whereas the inner portion of proximal part of the sheath (2) has a disk (2.4) whose central hole is crossed by a tube (4); one of the ends of tube (3) is lodged in a second hole that lies acentrically on the said disk (2.4).

5 Claims, 4 Drawing Sheets

INFLATABLE PROCTEURYNTER FOR TREATMENT OF ANAL SPHINCTER PATHOLOGIES

BACKGROUND OF THE INVENTION

1. Field of the invention

The invention is of valid use in the field of the treatment of anal sphincter pathologies, especially for the cure of fissures and sphincter hypertonia.

2. Description of the Prior Art

Anal manometry carried out in patients suffering from anal fissures has always shown that hypertonia of the anal sphincter at rest is the main cause of the pathology and its chronicity.

Many methods have been suggested for the treatment of anal fissures postanoplasty combined with sphincterotomy, internal lateral sphincterotomy and postanoplasty combined with sphincterotomy carried out gradually, i.e. not involving the entire thickness of the sphincter but sufficient to allow for its release.

However, these extremely valid treatments call for hospitalization for a period of two or three days, leading to higher costs for the community and an understandable sense of anxiety and unease in the patient.

A new technique known as hydropneumatic dilation has been recently introduced, allowing for out-patient treatment (no hospitalization required). To carry out said hydropneumatic dilation, an instrument sold under the name of "Dilatan" is currently used. It consists of a cone made of rigid plastic material that is filled with warm water; the apex of the instrument is introduced into the anal sphincter, whereas the cone is left outside. Rigid procteurynters of varied caliber are available on the market. However, "Dilatan" carries out simple sphincter gymnastics and not a divulsion.

As an alternative to "Dilatan", the use of an inflatable bag normally used for the dilation of colic anastomosis has been suggested.

Both the above mentioned instruments have the serious defect of being difficult to retain within the anal canal because of the difference in their shape and that of the anatomic area into which they are inserted.

SUMMARY OF THE INVENTION

The objective of the invention in question is to create an instrument for hydropneumatic dilation which is able to penetrate the anal canal relatively easily and anchor itself perfectly to the sphincter, greatly reducing the possibility of involuntary release.

The said objective and others are reached by the procteurynter in question, consisting of a small inflatable bag in plastic material and a sheath, most of the internal length of which is crossed by a tube for the eventual introduction of an ultrasonoscope. A second tube serves the purpose of transporting water or air into the bag.

The bag, which is preferably transparent and completely deflatable for positioning, is fixed to two cuffs (one distal and the other proximal) that adhere tightly to the sheath by means of glue or heatsealing.

When distended, the bag is generally peanut shaped with a constricted central neck. Clearly, other alternative shapes may also be created, as long as they have at least one inflatable cone to be inserted into the ampulla of the rectum, a constriction to be positioned within the anal sphincter and an external bulge.

The narrow portion (neck) of the peanut is reinforced by any means known in the prior art (using non-stretch material reinforcement or by increasing the thickness of the wall) and must have a diameter of 3–4 cm and a height of 2–3 cm. There must be a difference of 2–4 cm between the maximum diameter of the neck and the maximum diameter of the peanut. The maximum diameter of the two bulb portions of the peanut joined to the constricted neck must be 5–8 cm; the height of these two bulb portions may vary from 2–5 cm.

The end of the sheath to be inserted into the rectum is rounded in shape to facilitate introduction.

The walls of the sheath and that of the tube for the flow of water and air are strong enough to withstand compression stress. The wall of the second tube is very thin and, if the ultrasonoscope is not present within it, said tube tends to collapse during the input of water or air. To avoid this happening, the tube may be filled with a cylindrical rod.

The tube into which the ultrasonoscope is inserted is open only at the end that lies outside the bag. The proximal end of the tube, in which water or air to inflate the tube flows, has a pipe for connection to a special syringe (for example with screw coupling) or a faucet, whereas the distal end—which may or may not pass through a disk—terminates within the interstice of the sheath.

Said disk, placed inside the sheath, limits proximally the above mentioned interstice and may be positioned proximally or distally with respect to the proximal cuff of the bag. A tube for the introduction of the ultrasonoscope (if present) passes through the above mentioned disk. The instrument in question works perfectly even in the absence of the scope and relative tube.

The instrument in question allows for the execution of anal sphincter dilation in a calibrated and gradual manner. The first advantage of the use of said instrument consists in the possibility of treating the patient in the out-patient department, in a single sitting and, therefore, with hardly any cost to the health service. Another advantage lies in the simplicity of the technique which permits the patient to carry out his or her normal working activity with immediate resolution of most of the painful symptomatology.

BRIEF DESCRIPTION OF THE DRAWINGS

Further characteristics and advantages of the invention will appear more clearly from the description of a preferred, but by no means sole, embodiment of the inflatable procteurynter, illustrated for indicative and not restrictive purposes in the following drawings in which.

DETAILED DESCRIPTION OF THE PREFERRED EMBODIMENT

Figure 1:
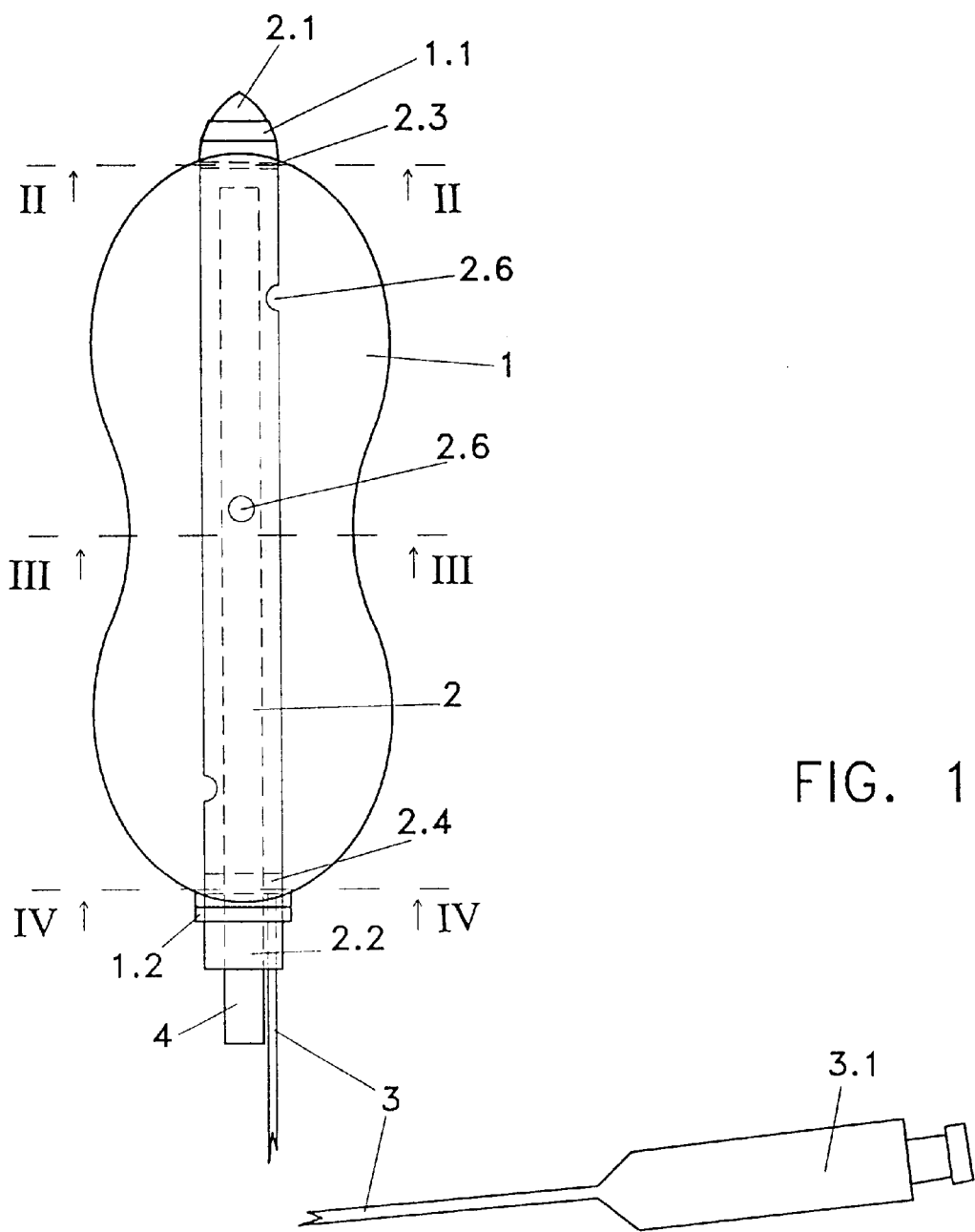
FIG. 1 shows a side view of the entire above mentioned procteurynter.
Figure 2:
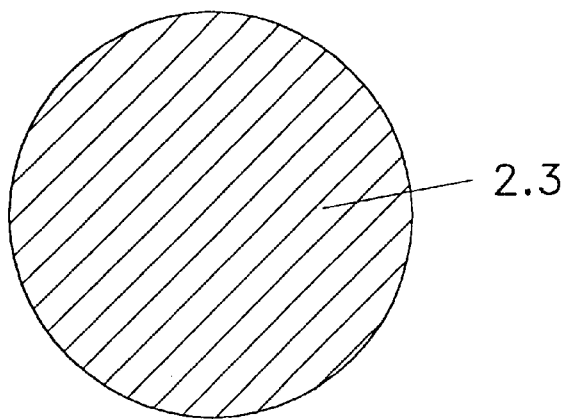
FIGS. 2, 3 and 4 show cross sections of the procteurynter represented in FIG. 1.
Figure 3:
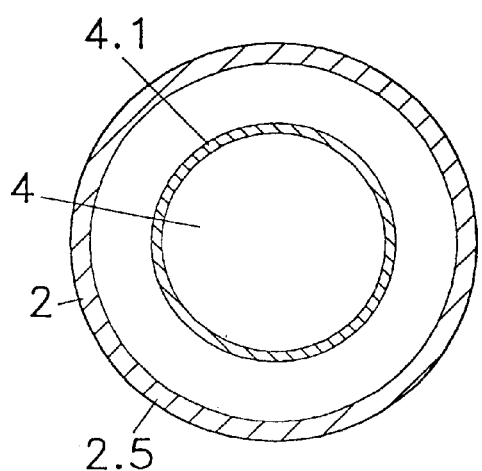
Figure 4:
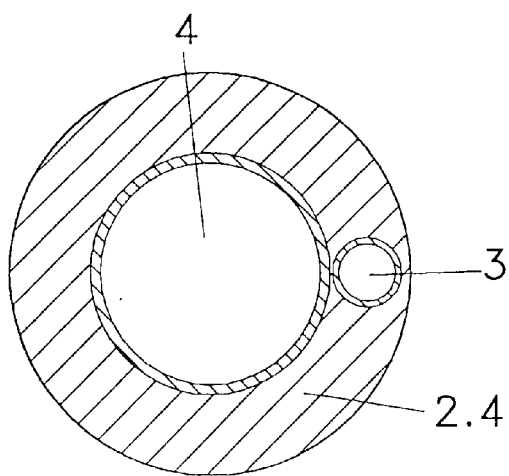
Figure 5:
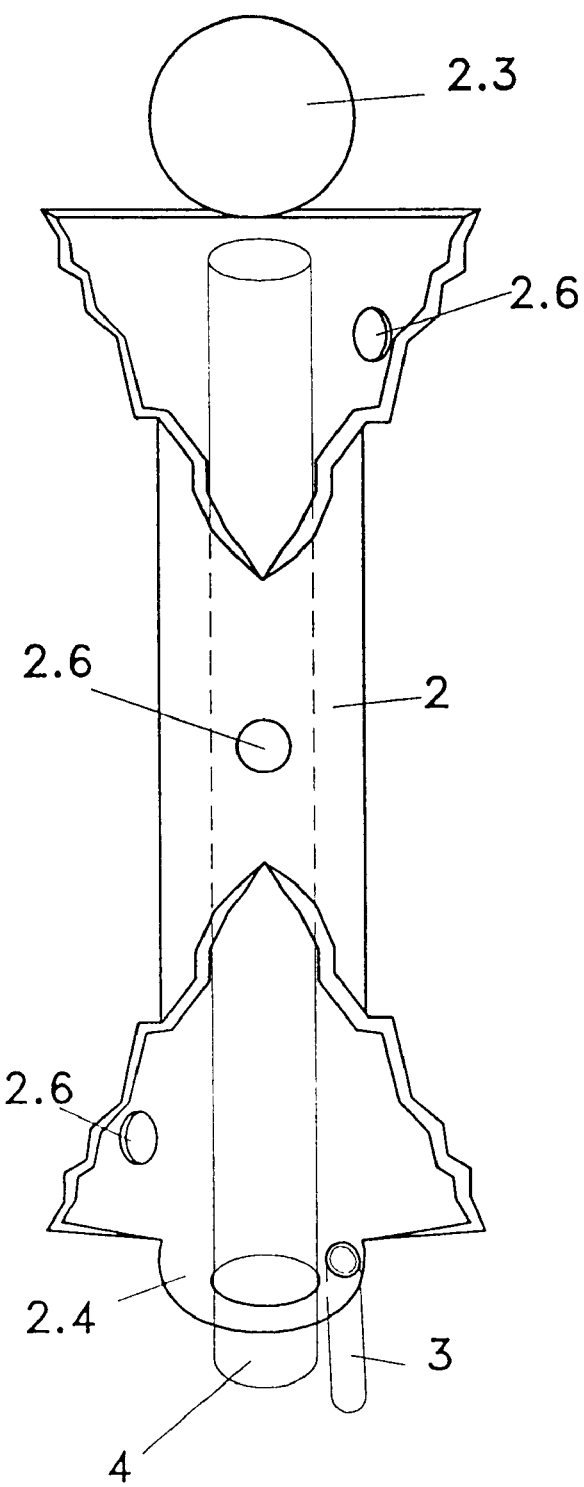
FIG. 5 shows a section plane of the sheath and its internal components in the area occupied by the bag.
Figure 6:
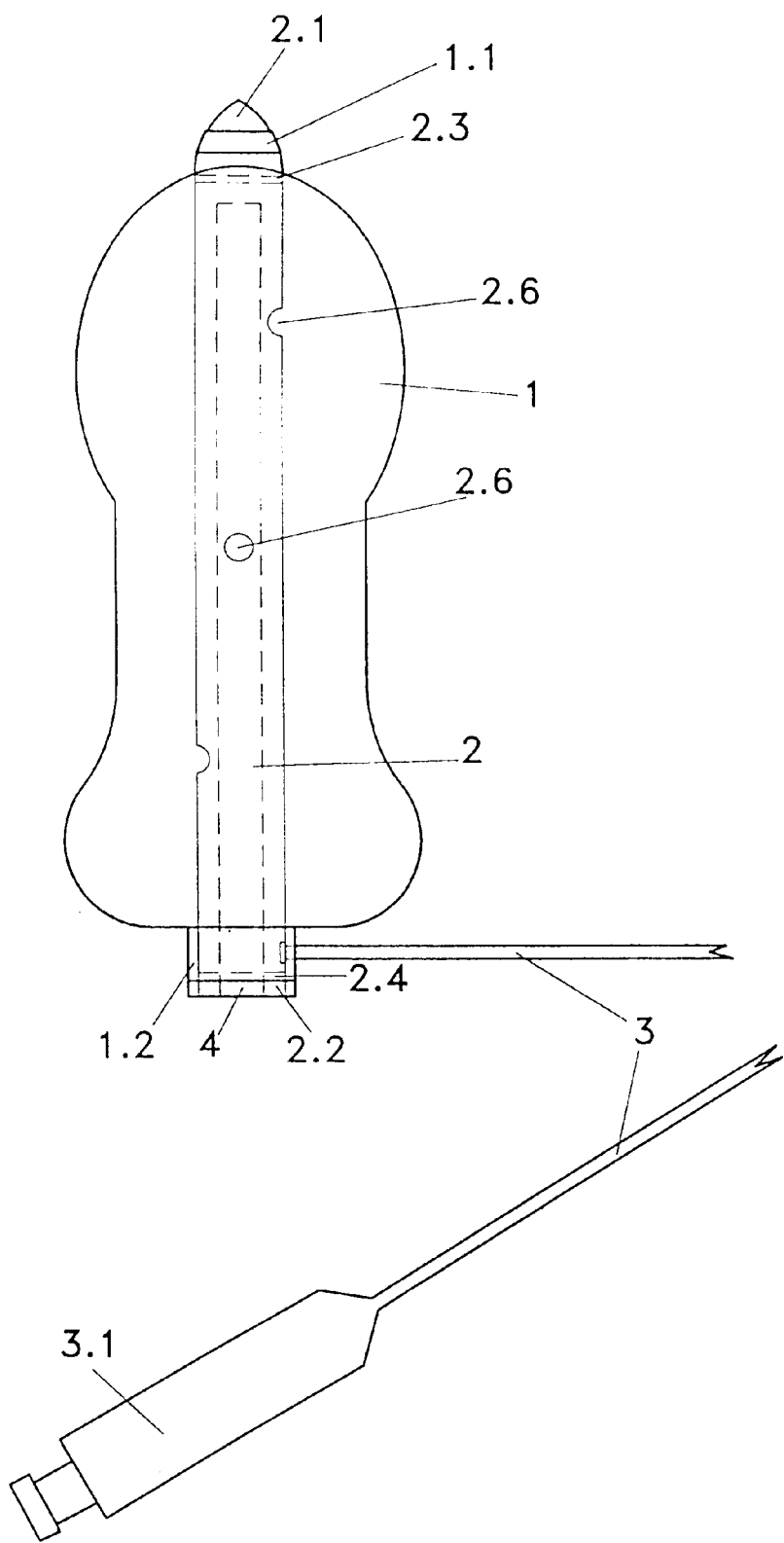
FIG. 6 illustrates a side view of an entire alternative embodiment of said procteurynter having a different shaped bag and a different arrangement of the tube for the flow of water or air.

More specifically, the procteurynter in question consists of a bag 1 made of plastic material and a sheath 2 internally crossed by a tube 4 for the insertion of an ultrasonoscope. A tube 3 allows for water to be transported into the bag 1.

The bag 1, which is preferably transparent, is fixed to two cuffs 1.1 and 1.2 which in turn adhere tightly to the sheath 2; fixing is carried out by heat sealing.

Once filled with water, the bag 1 takes on the shape of a peanut and is completely deflatable during positioning. The constricted central neck of the peanut is strengthened to limit the maximum diameter obtainable and has a diameter of 4 cm and a height of 3 cm. There is a difference of approximately 3 cm between the maximum diameter of the neck and the maximum diameter of the two bulb portions of the peanut joined to the constricted neck. Therefore, the maximum diameter of these bulb portions is 7 cm and the cones are not more than 5 cm in height.

As mentioned above, the sheath 2 is internally crossed by tube 4 and is slightly longer than the bag 1. In fact, only the ends of the sheath 2 protrude from the bag 1: a distal toe 2.1 and a proximal cuff 2.2.

The part of the sheath 2 inserted within the bag 1 has a special structure. More specifically, near the toe 2.1, and proximally with respect to the distal cuff 1.1, the sheath 2 has a plug 2.3 which occludes the lumen inside the sheath 2. Near the proximal cuff 1.2 (and distally placed with respect to it), lies a disk 2.4 whose central hole is crossed by a tube 4; the distal end of tube 3 is lodged in a second hole placed eccentrically on the disk 2.4.

Inside the part of the sheath 2 enclosed within the bag 1 is an interstice outside tube 4 limited internally by the wall 4.1 of the tube 4, externally by the wall 2.5 of the sheath 2, distally by the plug 2.3 and proximally by the disk 2.4. This interstice collects the water coming from tube 3 and, through special holes 2.6 made in the wall of the sheath 2, lets the water into the bag 1 which is thus inflated.

The walls 2.5 of the sheath 2 and of the tube 3 for the flow of water are strong enough to withstand the compression stress of water thrust. On the contrary, the wall 4.1 of tube 4 is very thin and, if the ultrasonoscope or a special cylinder is not present within the tube, the latter collapses during the inflow of water.

Tube 3 has a pipe 3.1 at its proximal end to allow for connection to a syringe or faucet.

Hydropneumatic dilation treatment using the above described instrument is carried out under local anesthesia with the patient placed in lithotomic position. A few minutes after administration of the anesthetic, the said procteurynter is inserted into the anal canal with the bag 1 completely deflated.

The toe 2.1 facilitates introduction.

Water from a syringe or faucet on tube 3 (by means of pipe connection 3.1) is then inlet. The water thrust by the compression force of the syringe or the water supply flows through tube 3, filling the interstice that lies inside the sheath 2 (which is limited, as described above, by the wall 4.1 of tube 4, the wall 2.5 of the sheath 2, the plug 2.3 and the disk 2.4) till it flows out of the sheath 2 through the holes 2.6 and fills the bag 1 which is thus inflated. When the bag 1 is completely filled with water, it must be in a specific position with the distal cone placed inside the ampulla of the rectum, the neck inside the anal sphincter and the proximal cone lying outside, between the patient's buttocks.

As the bag has the same conformation as the anatomical part in which it is lodged, it fits snugly, preventing its release.

The procteurynter in question is kept in this position for some minutes. After this period of time, the water is suctioned and flows out of the bag 1, the interstice of the sheath 2 and the tube 3 itself. The bag deflates and the said instrument is discharged and can eventually continue treatment at home using "Dilatan" for about 10 days until the typical symptoms of the pathology disappear.

Thanks to the way the device in question has been designed, various modifications can be made. Furthermore, all components may be replaced with similar ones having the same technical characteristics.

I claim:

1. Inflatable procteurynter for the treatment of anal sphincter pathologies comprising: a bag (1) made of plastic material and a sheath (2), a portion of the inner length of s aid sheath being crossed by a tube (4) for introduction of an ultrasonoscope, the sheath (2) having an interstice therein which is limited externally by a wall (4.1) of the tube (4) and internally by a wall (2.5) of the sheath (2), water or air being insertable by means of a tube (3) into said interstice; the water or air passes through said interstice inside the bag (1) by means of holes (2.6) in the wall (2.5) of the sheath (2); said bag (1) when filled with the water or air taking on a shape having two bulb portions joined to a constricted central neck, said constricted central neck being reinforced and having a diameter of 3–4 cm and a height of 2–3 cm, whereas there is a difference of 2–4 cm between a maximum diameter of the constricted central neck and a maximum diameter of the two bulb portions, the maximum diameter of the two bulb portions being between 5–8 cm and the height of the two bulb portions varying from 2–5 cm; said bag (1) being fixed to two cuffs (1.1) and (1.2) which in turn are fixed to the sheath (2) by means of gluing or heatsealing; the sheath (2) being slightly longer than the bag (1) so that a toe (2.1), which is rounded in shape and is insertable into a rectum, and a cuff (2.2) both protrude from the bag (1); said interstice being distally limited by an internal plug (2.3) which is situated proximally with respect to the distal cuff (1.1) and limited proximally by a disk (2.4) placed distally with respect to the proximal cuff (1.2); a central hole of the disk (2.4) being crossed by the tube (4), whereas a distal end of the tube (3) is lodged in a second eccentric hole made on the disk (2.4); the wall (2.5) of the sheath (2) and that of the tube (3) being strong enough to withstand compression stress caused by the thrust of the water or air, whereas the wall (4.1) of tube (4) is thin and, if the ultrasonoscope or a special cylindrical rod is not inserted tends to collapse during the inlet of the water or air; the tube (4) in which the ultrasonoscope is inserted being open only at one end that lies outside the bag (1); the tube (3) for the flow of water or air having a pipe (3.1) at an external end for connection to a special syringe or a faucet.

2. Procteurynter as in claim 1, wherein during distension of said bag (1) may take on different shapes as long as it has at least one inflatable bulb portion inserted within the ampulla of the rectum, a constricted central neck to be placed within the anal sphincter and an external bulge to avoid a dilator from being sucked up into the rectum.

3. Procteurynter as in claim 1, wherein said disk (2.4) is placed proximally with respect to the proximal cuff (1.2) and the distal end of said tube (3) for the flow of the water or air may be inserted into the interstice of the sheath (2) passing directly through the wall (2.5) of the sheath (2).

4. Procteurynter as in claim 1, wherein said tube (4) for the passage of the ultrasonoscope may be absent; wherein the central hole of the disk (2.4) may be crossed by the tube (3) for the flow of water or air.

5. Procteurynter as in claim 1, wherein the water or air is force fed into the tube (3) and fills the interstice inside the sheath (2) until the water or air is discharged from the holes (2.6) and fills the bag (1) which is thus inflated; wherein when the bag (1) is completely filled with water or air, it is in a specific position with one of said two bulb portions inside the ampulla of the rectum and the constricted central neck within the anal sphincter; the water or air is then suctioned out, leading to the deflation of the bag (1) and the removal of the procteurynter.

\* \* \* \* \*